United States Patent [19]

Hiroshi et al.

[11] Patent Number: 5,307,144
[45] Date of Patent: Apr. 26, 1994

[54] PHOTOMETER

[75] Inventors: Tamura Hiroshi; Tanaka Shigenori, both of Tokyo, Japan

[73] Assignee: Seikagaku Kogyo Kabushiki Kaisha, Tokyo, Japan

[21] Appl. No.: 984,535

[22] Filed: Dec. 1, 1992

[30] Foreign Application Priority Data

Dec. 2, 1991 [JP] Japan .................................. 3-341787

[51] Int. Cl.$^5$ ...................... G01N 21/27; G01N 21/01
[52] U.S. Cl. ..................................... 356/244; 356/246;
356/440; 250/576; 422/102; 436/165; 436/809
[58] Field of Search ............... 356/244, 246, 414, 432,
356/435, 439, 440, 319, 320; 250/576, 238, 429;
422/101, 102, 186, 109, 58, 61; 436/165, 809

[56] References Cited

U.S. PATENT DOCUMENTS

| | | | |
|---|---|---|---|
| 4,498,780 | 2/1985 | Banno et al. | 356/244 |
| 4,498,782 | 2/1985 | Proctor et al. | 356/440 |
| 4,545,958 | 10/1985 | Dopatka | 422/102 |
| 4,824,791 | 4/1989 | Ekholm et al. | 422/102 |
| 5,063,024 | 11/1991 | Partanen et al. | 356/240 |
| 5,102,623 | 4/1992 | Yamamoto et al. | 422/63 |
| 5,149,654 | 9/1992 | Gross et al. | 435/809 |

Primary Examiner—Richard A. Rosenberger
Assistant Examiner—Hoa Q. Pham
Attorney, Agent, or Firm—Dellett and Walters

[57] ABSTRACT

The present invention intends to generally maintain the microplate having added test samples in wells therein at even temperature for measuring biochemical or biological reaction accompanying changes in absorbance such as enzyme reaction. Monochromatic lights with various wave lengths from a light source 3 are transmitted through the test samples added to a plurality of wells in a microplate 1 to measure absorbance of the test sample. For this end, a metal plate 2 with good heat conductivity is substantially contacted with the bottom of each well in the microplate 1 and a perforated board 7 is disposed with an air space over the microplate 1 at the starting position thereof. Warmed air heated by a heater 17 is blown onto the microplate 1 through the perforated board 7 and is circulated along the metal plate 2 within a chamber 9.

2 Claims, 2 Drawing Sheets

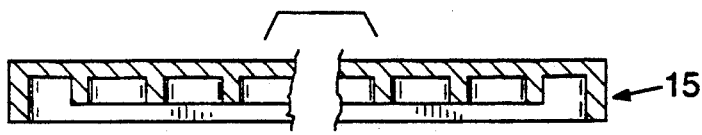
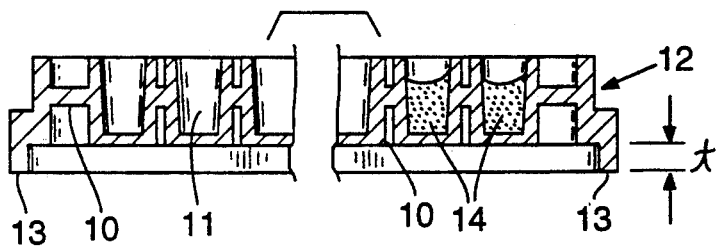
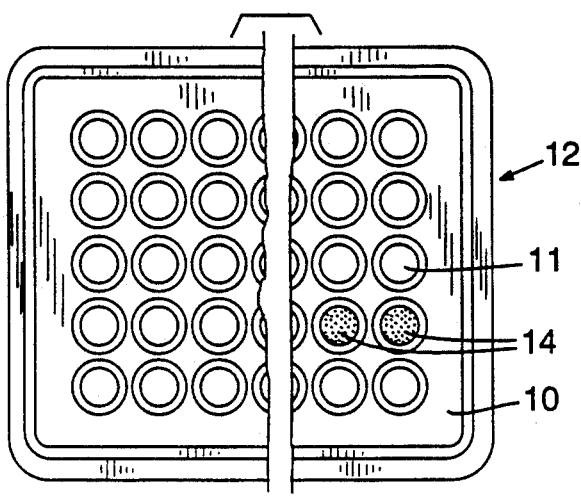
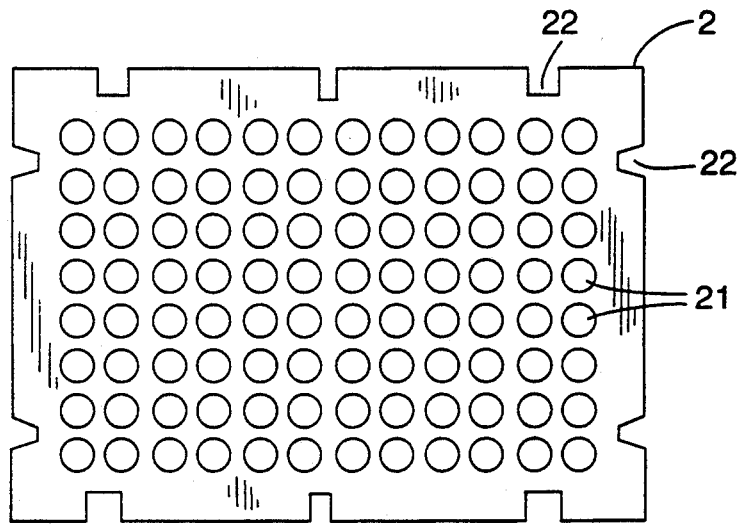
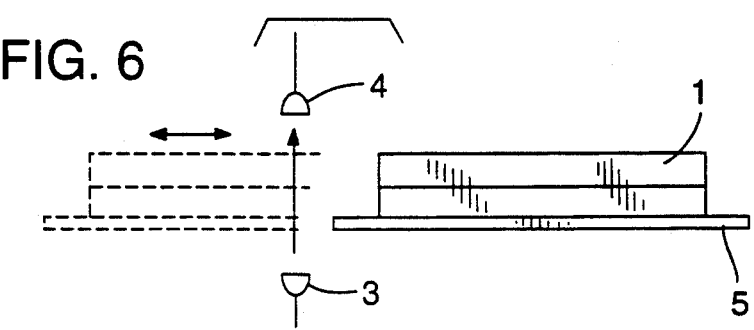

PHOTOMETER

BACKGROUND OF THE INVENTION

The present invention relates to an photometer for use in measuring biochemical or biological reaction accompanying changes in absorbance such a s enzyme reaction and the like, more specifically to one for evenly heating the microplate separately adding a test sample in wells and maintaining the temperature so that no temperature difference is present between wells.

As illustrated in FIG. 4(a), (b) and (c), a test sample 14 is added to each well 11 in a microplate comprising a lid part 15 made from a transparent synthetic resin and a wells part 12 made from a transparent synthetic resin and having a plurality of wells 11 inter-coupled with a plate member 10. The microplate is evenly heated to accelerate enzyme reaction and the like. Monochromatic lights with various wave lengths are transmitted to the test sample 14 during or after reaction to measure the absorbance of the test sample 14 in each well 11. Then, the biochemical or biological measurements such as the enzyme activity or quantitative measurements of the substrate in the test sample 14 are carried out based on the measured absorbance.

In other words, as illustrated in FIG. 6, a monochromatic light source 3 and a light detector 4 face each other. A microplate 1 containing the test sample 14 during or after reaction placed on a carrier 5 is transported between the light source 3 and the light detector 4. All test samples 14 in the wells 11 in the microplate 1 are scanned to measure absorbance and the absorbance values are related to the biochemical or biological reaction.

It is to be noted here that accurate and reproducible data cannot be obtained unless the absorbance measurements are carried out by maintaining the temperature of each test sample 14 in each well 11 in the microplate 1 even and constant. Otherwise, the reaction temperature condition differs for each test sample 14 in each well 11.

For this end, temperature control means are proposed to use a fan to enforcedly circulate warmed air so that the microplate 1 is evenly heated and maintained at constant temperature region without causing any temperature difference between wells.

However, in circulating warmed air within a chamber using a fan to stir air over the microplate 1, air flow on the surface of the microplate 1 partly differs; faster at the circumference and slower at the center portion.

This results in faster temperature rise at the circumference of the microplate 1 but slower at the center portion when the temperature of the microplate 1 in a chamber is to be raised by circulating the air. As a result, temperature difference between the test samples 14 in wells 11 in the microplate 1 is caused, thereby making it very difficult to obtain accurate and reproducible data due to uneven reaction temperature.

SUMMARY OF THE INVENTION

It is, therefore, the object of the present invention to overcome the above mentioned problem. The present invention is directed to a photometer for transmitting monochromatic lights with various wave lengths through test samples in a plurality of wells in a microplate for measuring the absorbance of the test samples and characterized in comprising a metal plate with good heat conductivity disposed substantially in contact with the bottom surface of each well in the microplate, a board having a plurality of openings therein and disposed with an air space over the microplate at the starting position thereof, air circulation means for enforcedly circulating air, and heating means to heat the air with all of the above constituents disposed in a chamber. Air is blown onto the upper surface of the microplate by way of the above-mentioned perforated board and is circulated along the metal plate with good heat conductivity.

BRIEF DESCRIPTION OF THE DRAWINGS

FIG. 4(a), (b) and (c) are a cross-section view of the lid part, a cross-section view of the wells part and a plan view of the wells part of the microplate to be used in the present and conventional photometer, respectively.

FIG. 5 is a plan view of an important part of another embodiment of the photometer in FIG. 1.

FIG. 6 is a side view of one example of a conventional photometer.

DETAILED DESCRIPTION OF PREFERRED EMBODIMENTS

Figure 1:
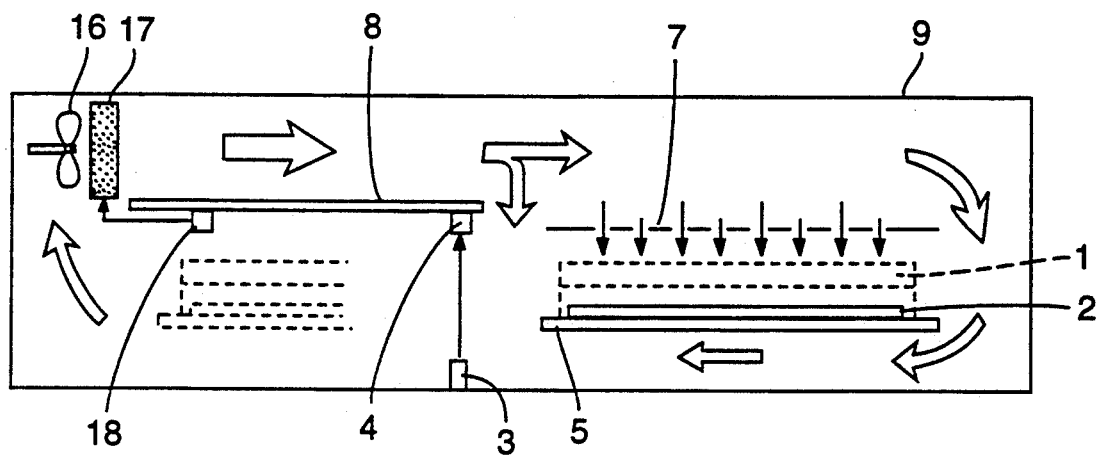
FIG. 1 is a side view of one embodiment of the photometer according to the present invention.

Illustrated in FIG. 1 is a photometer according to the present invention. The said photometer comprises a carrier 5 to place thereon a microplate 1, a reciprocally driving unit (not shown) to repeatedly move the carrier 5 in the horizontal direction, and absorbance measuring means (photometric unit) consisting of a light source 3 and a light detector 4 disposed facing each other at the upper and lower positions of the microplate 1 placed on the carrier 5, wherein all of the above constituents are disposed in a chamber 9.

Figure 2:
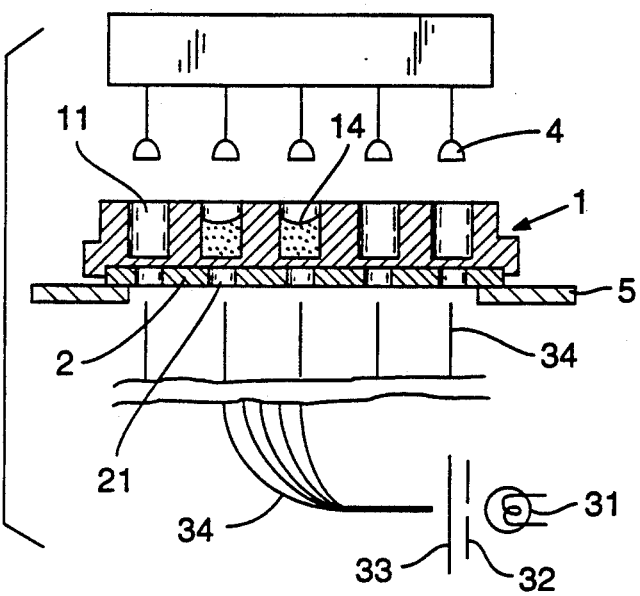
FIG. 2 is a cross-section view of a part of the photometer in FIG. 1.

The light source 3 in the absorbance measuring means comprises, as illustrated in detail in cross-section in FIG. 2, a light bulb 31, a slit 32, a plurality of filters 33 for passing lights with different wavelengths, and optical fibers 34 to split the monochromatic light selected by the filters 33 into a plurality of lights equal to the columns of wells 11 in the microplate 1. On the other hand, the light detector 4 comprises n number of photoelectric transducers 4 such as photo-transistors disposed in relation to the output ends of the optical fibers 34.

In order to enforcedly circulate the warmed air into the chamber 9, there are a heater 17, a fan 16 and a partition 8 to form a flow path. Additionally, there is provided a sensor 18 of high sensitivity and high precision to detect the circulating air temperature. The output from the sensor is used to control the heater 17 so as to maintain the constant temperature.

Figure 3:
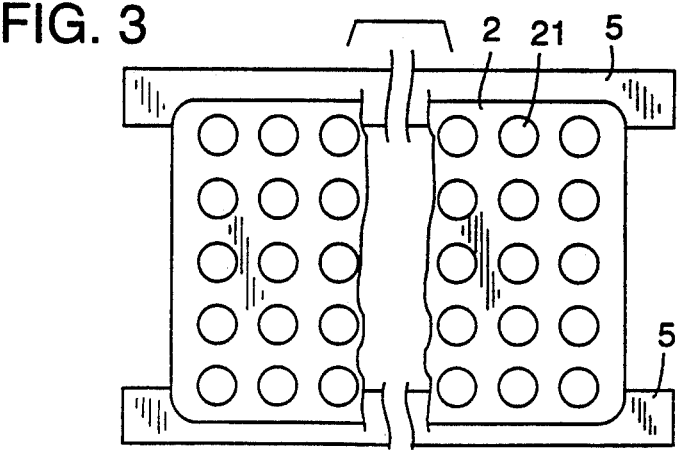
FIG. 3 is a plan view of an important part of the photometer in FIG. 1.

The microplate 1 is placed on a perforated aluminum plate 2 with good heat conductivity as illustrated in cross-section and plan views in FIG. 2 and 3, respectively. Openings 21 in the aluminum plate 2 are corresponded to the wells 11 in the microplate 1. The aluminum plate 2 is mounted on the carrier 5 by screws.

The perforated plate 2 with good heat conductivity is not limited only to the aluminum plate but may be duralumin, stainless steel, copper and the like. The size and shape of the plate may be selected to be adapted to the bottom of the microplate 1 so as to have the surface of the plate be substantially in contact with the bottom surface of the wells 11.

In other words, as illustrated in FIG. 4(b) there is provided a continuous pedestal portion 13 at the bottom circumference of the wells part 12 of the microplate 1. Since there is a little gap t between the bottom surface of the wells 11 and the bottom of the portion 13, the perforated plate 2 has preferably the size and shape so that the plate engages the inside of the continuous pedestal portion 13 and upper surface of the plate comes in contact with the bottom of the well 11.

Additionally, there is provided a perforated synthetic resin board 7 disposed on the microplate 1 with an air space.

The fan 16 and the heater 17 are operated in advance to circulate warmed air within the chamber 9. Subsequently, the test sample 14 is added to each well 11 in the microplate 1 and the wells 11 are covered with the lid part 15. The microplate 1 is then placed on the carrier 5 in such a manner that the perforated aluminum plate 2 substantially comes in contact with the bottom of each well 11.

The driving unit is run to repeatedly reciprocate the carrier 5 in the horizontal direction. Each test sample 14 added to each well 11 in the microplate 1 is allowed to pass between the light source 3 and the light detector 4 to measure and record the absorbance changes of each test sample 14. It is to be noted here that the filter 33 is switched to select different monochromatic light according to the kinds of the test sample 14 for measuring absorbance of the test sample.

A part of the warmed air by the heater 17 and circulated by the fan 16 during measurements is gently blown onto the upper surface of the microplate 1 by way of the perforated synthetic resin board 7. The other part of the air warmed flows between the bottom of perforated aluminum plate 2 under the bottom of the microplate 1 and the wall surface of the chamber 9.

As mentioned hereinbefore, the warmed air is gently blown onto the entire upper surface of the microplate 1 by way of the perforated synthetic resin board 7, thereby evenly heating the upper surface. Also, the perforated aluminum plate 2 has good heat conductivity on the whole bottom of the microplate 1, thereby generally heating the bottom of each well 11 all over the microplate.

Now, in a case of moving only the microplate 1 from the starting position to the measurement position and maintaining the plate 2 with good heat conductivity immovable, the plate 2 adapted to the bottom of the microplate 1 may not have openings 21. In this case, the good heat conductive plate 2 may be positioned at any suitable place for heating the microplate 1.

The number of wells (columns and rows) of the microplate 1 may be chosen to any desired value but is typically 96 (8×12).

Also, in manufacturing the microplate by injection molding, the microplate may have projections on the bottom due to molding die or mechanical strength. In this case, the perforated aluminum plate 2 with good heat conductivity may have cut-away portions 22 to receive the projections as illustrated in FIG. 5.

As understood from the above description of the preferred embodiments, the photometer according to the present invention can maintain all of the test samples 14 added to the wells 11 the microplate 1 at a uniform and accurate temperature, thereby constantly maintaining the reaction condition of each test sample required for accurate and reproducible data.

What is claimed is:

1. A photometer for transmitting monochromatic light with various wavelengths through test samples in a plurality of wells in a microplate for measuring the absorbance of the test samples, characterized in comprising a metal plate with good heat conductivity disposed substantially in contact with the bottom surface of each well of said microplate, a board having a plurality of openings therein and disposed with an air space over said microplate at a starting position thereof, air circulation means for enforcedly circulating air, and heating means to heat the air wherein said microplate, said metal plate and said board are disposed in a chamber, wherein air is blown onto the upper surface of said microplate by way of said board having openings and is circulate along said metal plate with good heat conductivity.

2. A photometer in accordance with claim 1 wherein said metal plate with good heat conductivity is formed with openings at the locations corresponding to the wells in said microplate under which said metal plate is placed.

* * * * *

UNITED STATES PATENT AND TRADEMARK OFFICE
CERTIFICATE OF CORRECTION

PATENT NO. : 5,307,144
DATED : April 26, 1994
INVENTOR(S) : Tamura Hiroshi; Tanaka Shigenori It is certified that error appears in the above-identified patent and that said Letters Patent is hereby corrected as shown below:

Column 1, line 7, "a s" should be --as--.

Column 3, line 37, "air warmed" should be --warmed air--.

line 37, "air warmed" should be --warmed air--.

Column 4, line 20, after "wells 11" insert --in--.

line 41, "circulate" should be --circulated--.

Signed and Sealed this

Thirtieth Day of August, 1994

*Attest:*

BRUCE LEHMAN

*Attesting Officer*     *Commissioner of Patents and Trademarks*